US007442398B2

United States Patent
Kim et al.

(10) Patent No.: US 7,442,398 B2
(45) Date of Patent: Oct. 28, 2008

(54) **PHYTASE PRODUCED FROM *CITROBACTER BRAAKII***

(75) Inventors: Young Ok Kim, Busan (KR); Han Woo Kim, Busan (KR); Jeong Ho Lee, Busan (KR); Kyung Kil Kim, Busan (KR); Jong Yun Lee, Busan (KR); In Soo Kong, Busan (KR)

(73) Assignee: Republic of National Fisheries Research and Development Institute, Busan (KR)

( * ) Notice: Subject to any disclaimer, the term of this patent is extended or adjusted under 35 U.S.C. 154(b) by 0 days.

(21) Appl. No.: 10/550,758

(22) PCT Filed: Mar. 25, 2004

(86) PCT No.: PCT/KR2004/000680

§ 371 (c)(1),
(2), (4) Date: Sep. 23, 2005

(87) PCT Pub. No.: WO2004/085638

PCT Pub. Date: Oct. 7, 2004

(65) Prior Publication Data

US 2006/0194298 A1 Aug. 31, 2006

(30) Foreign Application Priority Data

Mar. 25, 2003 (KR) .................. 10-2003-0018573

(51) Int. Cl.
*A23L 1/36* (2006.01)
*C12N 9/16* (2006.01)
*C12P 19/30* (2006.01)
*C12P 21/06* (2006.01)
*C07H 21/02* (2006.01)
*C07H 21/04* (2006.01)
*A23C 9/121* (2006.01)

(52) U.S. Cl. ................. 426/630; 426/63; 435/21; 435/69.1; 435/91.1; 435/196; 536/23.1; 536/23.2

(58) Field of Classification Search ............... 435/195, 435/69.1, 252.3; 424/93.1; 426/56; 536/23.2
See application file for complete search history.

(56) References Cited

U.S. PATENT DOCUMENTS 6,235,517 B1    5/2001    Chu et al.

FOREIGN PATENT DOCUMENTS

EP    0779037 A1    6/1997

OTHER PUBLICATIONS

Kim et al., Isolation and characterization of a phytase with improved properties from *Citrobacter braakii*. Biotechnol. Letters., 2003, vol. 25: 1231-1234.*
Kim et al., Purification and characterization of a novel phytase from *Citrobacter brakii* YH-15 strain. 9th International Symposium on the Genetics of Industrial Microorganisms. Abstract P21-31, Jul. 1-5, Gyeonju, Korea (In IDS).*
Lei, X.G, & Stahl, C.H., "Biotechnological development of effective phytases for mineral nutrition and environmental protection," Appl Microbiol Biotechnol (2001) 57:474-481.
Kim, H.W, et al., "Isolation and characterization of a phytase with improved properties from *Citrobacter braakii*,"Biotechnol. Lett., Aug. 2003, 25:1231-1234.
Kim, Young-Ok et al., "Purification and characterization of a novel phytase from *Citrobacter braakii* YIL-15" Abstract P21-31 from 9th International Symposium on the Genetics of Industrial Microorganisms, Jul. 2002.
Ullah, Abul H.J., et al., "Characterization of recombinant fungal phytase (phyA) expressed in tobacco leaves,"Biochemical and Biophysical Research Communications (1999) 264(1):202-206.

* cited by examiner

*Primary Examiner*—Rebecca E. Prouty
*Assistant Examiner*—Ganapathirama Raghu
(74) *Attorney, Agent, or Firm*—Joseph Hyosuk Kim; JHK Law

(57) ABSTRACT

The present invention relates to phytase enzyme, a gene encoding the enzyme, and a *Citrobacter* sp. producing the enzyme. Particularly, the present invention relates to the phytase enzyme produced from *Citrobacter* sp. having (a) molecular weight of 47 kDa, (b) optimal pH of 3.5-4.5, (c) optimal temperature of 45-55° C., (d) a substrates phytate, p-nitrophenyl phosphate, tetrasodium pyrophosphate, ATP or ADP, (e) Michaelis constant of 0.3-0.5 mM utilizing phytate as substrate, and (f) high resistance to protease such as pepsin, trypsin, papain, elastase or pancreatin. The present invention also relates to the gene coding the phytase enzyme and the *Citrobacter braakii* producing the enzyme. The phytase enzyme and the *Citrobacter braakii* producing the enzyme of the present invention can be used in manufacturing a feed of monogastrics as feed additive and in recovering a specific decomposition product of phytate at low price.

10 Claims, 5 Drawing Sheets

PHYTASE PRODUCED FROM *CITROBACTER BRAAKII*

FIELD OF THE INVENTION

The present invention relates to a novel phytase enzyme, a gene coding the enzyme, a *Citrobacter* sp. strain producing the enzyme and a feed additive containing the protein or the strain as an effective ingredient.

BACKGROUND

Phytase is an enzyme decomposing phytic acid (myo-inositol 1,2,3,4,5,6 hexakis dihydrogen phosphate) to produce phosphate and phosphate inositol. Phytic acid takes 50~70% of phosphorus contained in animal feed grains. However, monogastric animals such as fish, fowls and pigs do not have phytase decomposing phytic acid inside body, so that a coefficient of utilization of vegetable phosphorus, which is necessary for growth, is very low, requiring an enough supply from outside body in the form of inorganic compounds. Phytic acid included in feed grains, which is not digested in monogastric animals, can be decomposed enzymatically by microorganisms in soil or in water while it is in transit to the river and the lake. So, the mass-inflow of phosphorus into underwater environment, where only restricted phosphorus is allowed, causes eutrophication inducing a lack of oxygen and a growth of seaweeds. Phytic acid becomes useless after chelating with important trace minerals, amino acids, vitamins, etc, which means it cannot be used in vivo after then, making it an anti-nutrition factor causing a huge nutrition loss in a feed. Thus, if phytase is added to a feed grains for monogastric animals, the useless phytic acid now can be useful, resulting in 1) beneficial reduction of inorganic phosphorus supply, 2) increase of coefficient of utilization of trace bioactive materials, and 3) reduction of phosphorus in animal feces, by which environmental pollution can be reduced. Therefore, the addition of phytase is not only important in economic aspects but also meaningful in environmental protection. Benefits including economic effect of adding phytase are very helpful for preparing globalization.

European countries have been leading the studies on phytase, so far (A. H. J. Ullah, et al., Biochem. Biophys. Res. Commun. 1999, 264, 201-206; K. C. Ehrich, et al., Biochem. Biophys. Res. Commun. 1994, 204(1), 63-68; C. S. Piddington, et al., Gene, 1993, 133(1), 55-62). In particular, they have studied on the effect and functions of phytase extracted from fungi (*Aspergillus* sp.) in monogastric domestic animals and fish (L. G. Young, et al., J Anim Sci 1993, 71(8), 2147-2150; K. D. Roberson, et al., Poult Sci 1994, 73, 1312-1326; N. Simoes, et al., Reprod Nutr Dev, 1998, 38, 429-440; M. Rodehutscord, et al., Arch Tierernahr 1995, 48, 211-219). However, they had troubles in those studies, for example, the amount of phosphorus digested by phytase was limited, the production of phytase was not economical since it was produced mainly in fungi having a long growth term, and the manipulation was troublesome.

Thus, in order to produce a novel phytase having as excellent activity as or different characteristics from the conventional phytase, the present inventors isolated a novel microorganim producing phytase from thousands of strains gathered from seawater and wastewater treatment plants all over the country and identified thereof. The present inventors completed this invention by confirming that phytase produced by the above microorganism of the invention was a novel protein having a novel base sequence and an excellent titer.

SUMMARY OF THE INVENTION

It is an object of this invention to provide a novel protein decomposing phytic acid produced from a *Citrobacter* sp. strain and a gene coding the protein.

It is also an object of this invention to provide a *Citrobacter braakii* strain producing the above protein.

It is a further object of this invention to provide a feed additive containing the above protein or the above strain as an effective ingredient.

DETAILED DESCRIPTION OF PREFERRED EMBODIMENTS

In order to achieve the above object, the present invention provides a protein produced from a *Citrobacter* sp. Strain and having physicochemical characteristics as follows.

(a) Molecular weight: about 47 kDa on SDS-PAGE,
(b) Optimal pH: pH 3.5-pH 4.5,
(c) Optimal temperature 45° C.-55° C.,
(d) Substrate specificity: phytate, p-nitrophenyl phosphate, tetrasodium pyrophosphate, ATP or ADP,
(e) Michaelis constant of 0.3-0.5 mM utilizing phytate as a substrate,
(f) High resistance to protease such as pepsin, trypsin, papain, elastase or pancreatin.

The present invention also provides a gene coding the above protein.

The present invention also provides a *Citrobacter braakii* strain producing the above protein.

The present invention further provides a feed additive containing the above protein or the above strain as an effective ingredient.

Hereinafter, the present invention is described in detail.

The present invention provides a novel protein decomposing phytic acid produced from a *Citrobacter* sp. strain.

The protein having an activity of decomposing phytic acid was named "phytase".

The phytase of the present invention is characterized by having the physicochemical characteristics as follows.

(a) Molecular weight: about 47 kDa on SDS-PAGE,
(b) Optimal pH: pH 3.5-pH 4.5,
(c) Optimal temperature 45° C.-55° C.,
(d) Substrate specificity: phytate, p-nitrophenyl phosphate, tetrasodium pyrophosphate, ATP or ADP,
(e) Michaelis constant of 0.3-0.5 mM utilizing phytate as a substrate,
(f) High resistance to protease such as pepsin, trypsin, papain, elastase or pancreatin.

Phytase of the present invention is an enzyme having phytase activity, which is originated from *Citrobacter* sp. strain and can be separated and purified after culturing the strain by using ammonium sulfate precipitation, phenyl separose, DEAE-separose, CM-separose and Mono S HR 5/5 column.

The phytase has a molecular weight of 47 kDa on SDS-PAGE and is activated by using phytate, p-nitrophenyl phosphate, tetrasodium pyrophosphate, ATP or ADP as a substrate. The phytase is an acidic enzyme showing a high enzyme activity at 45° C.-55° C. (optimal activity is observed at 50° C.) The enzyme activity is very stable between pH 3.0 and pH 7.0, the best activity can be seen between pH 3.5 and pH 4.5, and the optimal pH is 4.0. The enzyme activity is strongly inhibited by $Fe^{3+}$, $Zn^{2+}$ and $Cu^{2+}$ of various metal ions. Km value to phytate is 0.46 mM, and Vmax value is 6,027 U/mg. Besides, the phytase shows a strong resistance against many proteases such as pepsin, trypsin, papain, elastase or pancreatin (see FIG. 4, Table 5 and Table 6).

The phytase of the present invention is produced from *Citrobacter* sp. strain, and is preferably produced from *Citrobacter braakii*. More particularly, it is more preferable for the phytase of the present invention to be produced from *Citrobacter braakii* YH-15 (Accession No: KCCM 10427).

The phytase has an amino acid sequence represented by SEQ. ID. No 2 or a N-terminal amino acid sequence containing a sequence represented by SEQ. ID. No 2 in which one or more amino acids are replaced, deleted or added. The amino acid sequence is quite different from that of conventional phytase enzyme, so that it has been confirmed that the phytase of the present invention is a novel enzyme.

It is more preferable for the phytase of the present invention to include not only a N-terminal amino acid sequence represented by SEQ. ID. No 2 but also an amino acid sequence represented by SEQ. ID. No 7 or to have at least 70% homology with the sequences.

It is also preferred for the phytase of the present invention to have more than 1,500 U/mg of specific activity to phytate and is more preferred to have over 3,000 U/mg of specific activity.

The present invention also provides a gene coding the above protein.

It is preferable for the gene to code an amino acid sequence represented by SEQ. ID. No 7 or at least to code an amino acid sequence having more than 70% sequence homology with the above sequence. It is more preferable for the gene to have a base sequence represented by SEQ. ID. No 6 or to have a base sequence having more than 70% sequence homology with the above.

The phytase of the present invention has an open reading frame for a phytase composed of 1302 bases, and the open reading frame is composed of a signal sequence consisting of 22 amino acids and an active phytase represented by SEQ. ID. No 7 and consisting of 411 amino acids. The molecular weight of an active protein without a signal sequence is about 47,000 Da.

Base sequence of the phytase of the present invention is available for the production of a recombinant protein. For example, the base sequence can be included in various expression vectors for producing an enzyme. And those expression vectors include SV 40 inducer, bacterial plasmid, phage gene, Baculovirus, yeast plasmid, recombinant vector constructed by combining a plasmid with phage gene, viral gene, chromosome, non-chromosome and a synthesized base sequence.

Appropriate host cells can be transfected with the expression vectors to produce a target protein.

*Escherichia, Serratia, Corynebacterium, Brevibacterium, Pseudomonas, Bacillus, Aspergillus, Rhizopus, Trichoderma, Neurospora, Mucor, Penicillium, Chluiveromyces, Saccharomyces, Schizosaccharomyces, Pichia* sp. are good for host cells.

The present invention further provides *Citrobacter braakii* producing the protein.

*Citrobacter braakii* YH-15 (Accession No: KCCM 10427) is preferably chosen for *Citrobacter braakii* producing the phytase of the present invention.

The present inventors separated strains, which can produce a phytase decomposing phytate, from a sample taken from seawater and wastewater treatment plants near Busan, Korea. Activities of phytase produced in the strains were measured. And a strain showing the highest phytase activity was identified by using 16S rRNA sequence analysis and API kit. As a result, the strain of the present invention was confirmed to be a novel strain having 16S rRNA consisting of a base sequence represented by SEQ. ID. No 1, which had 99.0% homology with that of *Citrobacter braakii* and 98% homology with those of *Citrobacter freundii, Citrobacter werkmanii* and *Enterobacter aerogenes*.

The strain was a Gram-negative, rod-type bacterium having a cell size of 0.5~1.4 μm and had a flagellum (see FIG. 1). From the investigation of biochemical and physiological characteristics of the strain, the strain was confirmed to be a facultative microorganism, meaning that it could be growing with or without air, was positive to ornithin decarboxylase, and had an ability of citrate utilization but was negative to indole generation, acetone generation, hydrogen sulfide generation, gelatin liquefaction and lysine decarboxilase (see Table 2).

Based on the results of 16S rDNA analysis and morphological and physiochemical characteristics of the strain, the present inventors identified the strain separated in the present invention to be a novel *Citrobacter brakii*, which was then named "*Citrobacter braakii* YH-15" and was deposited at Korean Culture Center of Microorganisms (KCCM), on Sep. 26, 2002 (Accession No: KCCM 10427).

The present invention also provides a feed additive containing the protein produced from *Citrobacter braakii* or from the strain of the present invention.

The feed additive of the present invention preferably contained *Citrobacter braakii* (Accession No: KCCM 10427) or phytase produced from the strain as an effective ingredient. The feed additive of the present invention can be effectively used for the production of animal feeds since it contained phytase enhancing utilization of phosphorus in feeding grains.

The feed additive of the present invention can be prepared in the form of dried or liquid formulation, and can additionally include one or more enzyme preparations. The additional enzyme preparation can also be in the form of dried or liquid formulation and can be selected from a group consisting of lipolytic enzymes like lipase and glucose-producing enzymes such as amylase hydrolyzing α-1,4-glycoside bond of starch and glycogen, phosphatase hydrolyzing organic phosphate, carboxymethylcellulase decomposing cellulose, xylanase decomposing xylose, maltase hydrolyzing maltose into two glucoses and invertase hydrolyzing saccharose into glucose-fructose mixture.

The feed additive of the present invention can additionally include other non-pathogenic microorganisms, in addition to phytase or a microorganim producing phytase. The additional microorganism can be selected from a group consisting of *Bacillus subtilis* that can produce protease, lipase and invertase, *Lactobacillus* sp. strain having an ability to decompose organic compounds and physiological activity under anaerobic conditions, filamentous fungi like *Aspergillus oryzae* (Slyter, L. L., *J. Animal Sci.* 1976, 43. 910-926) that increases the weight of domestic animals, enhances milk production and helps digestion and absorptiveness of feeds, and yeast like *Saccharomyces cerevisiae* (Jhonson, D. E., et al., *J. Anim. Sci.*, 1983, 56, 735-739; Williams, P. E. V., et al., 1990, 211).

BRIEF DESCRIPTION OF THE DRAWINGS

The application of the preferred embodiments of the present invention is best understood with reference to the accompanying drawings, wherein.

Figure 1:
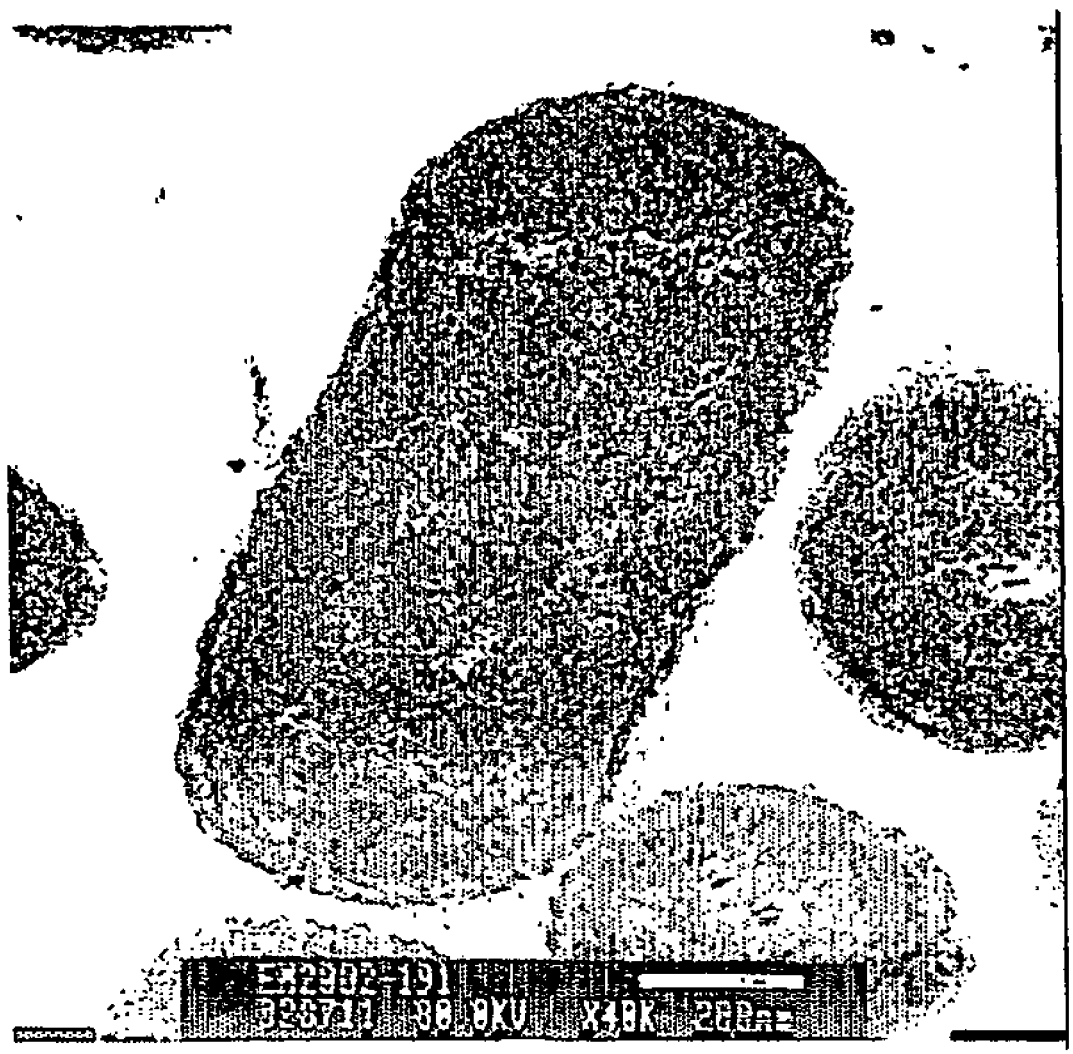
FIG. 1 is an electron microphotograph showing the *Citrobacter braakii* cell.

Lane 1: EcoRI and XhoI treated,
Lane 2: EcoRI treated,
Lane 3: SphI treated,
Lane 4: BamHI and HindIII treated,
Lane 5: EcoRI and HindIII treated,
Lane 6: EcoRI and BamH I treated,
Lane 7: PstI treated

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Separation of Phytase-producing Strains

The present inventors separated phytase-producing strains from samples taken from seawater and wastewater treatment plants near Busan, Korea. Particularly, in order to find phytase-producing strains, samples were taken from wastewater treatment plants near entry of Gwanganli beach and seawater near Busan, Korea, for example, Songjung, Haeundae, Daebyun, Sinsundae, Iegidae, Nakdong estuary, etc. The samples were smeared on artificial seawater plate media, followed by cultivation in a 30° C. incubator for 18 hours. Then, different colonies in various forms were selected. Each colony was smeared on PSM medium (1.5% D-glucose, 0.5% calcium phytate, 0.5% $NH_4NO_3$, 0.05% $MgSO_4 \cdot 7H_2O$, 0.05% KCl, 0.001% $FeSO_4 \cdot 7H_2O$, 0.01% $MnSO_4 \cdot 4H_2O$) containing 1.5% agar, followed by cultivation at 30° C. for 2 days. Strains having clear zones, which were generated around colonies, were primarily selected. The selected strain was inoculated in 5 ml of artificial seawater and PSM medium, which were cultured in a 30° C. shaking incubator for 24 hours. Phytase activities in the culture solution and in cell precipitate were measured and 5 out of the selected strains, which showed high phytase activity, were secondly selected. The present inventors named the 5 selected strains as 'YH-11', 'YH-13', 'YH-15', 'YH-60' and 'YH-103' of our own accord.

The present inventors measured the activity of phytase produced by the 5 strains above (Table 1). Inorganic phosphorus quantitative method of Fiske, et al. was used for measuring the activity of phytase in culture solution and in cell precipitate. Particularly, 400 μl of substrate solution (2 mM sodium phytate in 0.1 M sodium acetate buffer, pH 5.0) was added to 100 μl of enzyme solution diluted by required dilution ratio, which was reacted at 37° C. for 30 minutes. Then, 500 μl of 5% TCA solution was added thereto, which was just left at 0° C. for 10 minutes to stop the reaction. As for a control (blank), TCA (trichloroacetic acid) solution was added to enzyme solution to inactivate the enzyme and then substrate solution was added thereto, which was left for a while. 4 ml of reagent A (1:1:1:2 ratio of 6 N $H_2SO_4$/2.5% ammonium molybdate/10% ascorbic acid/$H_2O$) was added, followed by reaction at 37° C. for 30 minutes. Then, activities in enzyme solution and in a control were measured at 820 nm. 1 unit of the enzyme was determined to be the enzyme amount releasing 1 μmole of phosphate for 1 minute.

From measuring the phytase activity, it was confirmed that phytase produced by YH-15 strain had the highest enzyme activity (Table 1).

TABLE 1

| Activity of phytase produced by the selected strain | | | | | |
|---|---|---|---|---|---|
| Strain | YH-11 | YH-13 | YH-15 | YH-60 | YH-103 |
| Phytase activity | 0.048 U/ml | 0.041 U/ml | 0.074 U/ml | 0.052 U/ml | 0.044 U/ml |

Example 2

Analysis of Characteristics of YH-15 Strain Producing a Phytase

The present inventors analyzed characteristics of YH-15 strain, which was separated in the above Example 1, producing a phytase having the highest enzyme activity.

YH-15 strain was confirmed to be a gram-negative bacterium through Gram staining. The strain was a rod type bacterium having a flagellum and the cell size was 0.5~1.4 μm, which was observed under an electron microscope (FIG. 1). The present inventors further investigated biochemical and physiological characteristics of the strain. As a result, the strain was a gram-negative, facultatively aerobic microorganism that could be growing with or without oxygens and showed positive reaction to ornithin decarboxilase but was negative to indole generation. Other biochemical and physiological characteristics of the strain were shown in Table 2. The present inventors also analyzed 16S rRNA sequence of the strain, resulting in that the strain had a base sequence represented by SEQ. ID. No 1 and the base sequence of 16S rRNA showed 99% homology with that of *Citrobacter braakii* and 98% homology with sequences of *Citrobacter freundii, Citrobacter werkmanii* and *Enterobacter aerogenes*.

Based on the results of investigation on morphological, physiological and biochemical characteristics and 16S rDNA of the strain, the present inventors identified the strain as a novel *Citrobacter braakii*.

The present inventors named the strain "*Citrobacter braakii* YH-15" and deposited it at Korean Culture Center of Microorganisms (KCCM), on Sep. 26, 2002 (Accession No: KCCM 10427).

TABLE 2

Characteristics of *Citrobacter braakii* YH-15

| Characteristics | *Citrobacter braakii* YH-15 |
|---|---|
| Gram-staining | Negative |
| Morphology and size | 0.5 × 1.4 μm |
| Mobility | + |
| Citrate utilization | + |
| Indole generation | − |
| Acetone generation | − |
| Hydrogen sulfide generation | − |
| Gelatin liquefaction | − |
| Ornithin decarboxilase | + |
| Lysine decarboxilase | − |

Example 3

Separation and Purification of Phytase Produced by *Citrobacter braakii* YH-15

In order to purify the phytase produced by *Citrobacter braakii* YH-15 strain identified in the above Example 2, the present inventors cultured the strain under the optimal culture conditions and separated the enzyme.

<3-1> Production of Phytase

*Citrobacter braakii* YH-15 of the present invention was cultured in LB medium containing 1% tryptone, 0.5% yeast extract and 0.5% NaCl at 30° C. for 15 hours, which was called seed-culture solution. The seed-culture solution was inoculated again (1%) to produce the enzyme. The phytase activity was measured with the same method as used in the above Example 1. As a result, the highest phytase activity was observed 16 hours later and at that time the produced enzyme was 0.2 unit/ml.

<3-2> Separation and Purification of Phytase

The present inventors purified phytase produced by *Citrobacter braakii* YH-15. Particularly, cells collected by centrifugation after being cultured in the above Example <3-1> were dissolved in 20 mM sodium acetate (pH 5.0) buffer solution, followed by crushing with a cell homogenizer (30 kHz, 30 minutes). Supernatant was obtained by centrifugation with 12,000 g for 20 minutes. Ammonium sulfate powder was added to the supernatant, leading to 70% saturation, followed by centrifugation with 12,000 for 20 minutes. Then, precipitate was obtained. Sodium acetate buffer solution (pH 5.0) was added to the precipitate to dissolve it. Dialysis was performed by using the same buffer solution. After dialysis, the solution was centrifuged and supernatant was obtained. Finally, phytase was purified through phenyl-, DEAE- and CM-Sepharose column and Mono S HR 5/5 column.

First, purification by using phenyl-sepharose column was as follows. Phenyl-sepharose column was equilibrated with sodium acetate buffer solution (pH 5.0) supplemented with 1.5 M ammonium sulfate. Enzyme extract solution containing the same amount of ammonium sulfate was added thereto. Then, the column was washed enough with the same buffer solution. While the buffer solution was added to the column, the concentration of ammonium sulfate decreased from 0.5 M to 0 M degree by degree in order to elute bound proteins gradually. 0.3 M ammonium sulfate was used to elute phytase.

Second, purification by using DEAE column was as follows. Phytase solution, which was obtained through phenyl-sepharose column, was equilibrated with tris buffer solution (50 mM Tris-HCl, pH 8.0) by dialysis. The phytase solution was added to DEAE-sepharose column that was equilibrated with the same buffer solution. The same buffer solution was continuously added to separate non-binding fractions showing high phytase activity. The fractions were concentrated and 20 mM sodium acetate (pH 5.0) was used for CM-sepharose column. After washing the column enough with the same buffer solution, bound proteins were eluted by increasing the concentration of NaCl from 0 M to 1 M gradually. At that time, 0.6 M of NaCl was used to elute the proteins.

Lastly, chromatography was performed by using Mono S HR 5/5 FPLC column with the same buffer solution that was used in the purification by using CM-sepharose column. At that time, 0.1 M NaCl was used to elute phytase and the separated phytase was finally purified.

<3-3> Measurement of Phytase Activity

Figure 2:
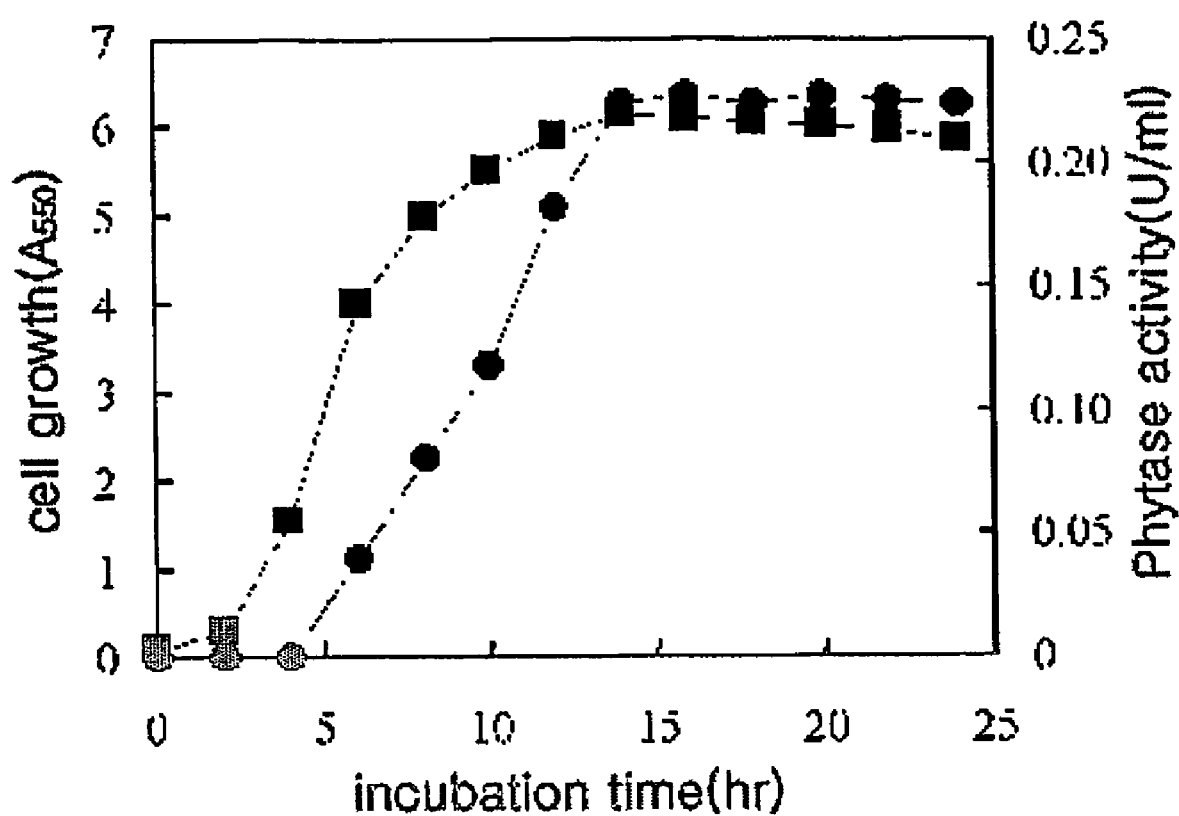
FIG. 2 is a graph showing the cell growth and the enzyme activity of phytase produced from *Citrobacter braakii* YH-15.

The enzyme activity of phytase included in each sample prepared from each purification stage of the above Example <3-2> was investigated (Table 3). Protein content was quantified by BCA protein quantification kit provided by Sigma, co. At that time, BSA (bovine serum albumin) was used as a standard protein. Specific activity of the purified phytase to phytate was 3,457 units/mg, recovery rate was 28%, and the final phytase was purified by 12,950 fold (FIG. 2).

TABLE 3

Total content, activity, purification rate and recovery rate of phytase purified from *Citrobacter braakii* YH-15

| Purification stage | Total activity (U) | Total content (mg) | Specific activity (U/mg) | Concentration (fold) | Recovery rate (%) |
|---|---|---|---|---|---|
| Cell homogenate | 1,453 | 5,443 | 0.27 | 1.00 | 100 |
| Ammonium sulfate precipitate | 1,380 | 1,593 | 0.87 | 3.25 | 95 |
| Phenyl-sepharose | 941 | 72.19 | 13.04 | 48.85 | 65 |
| DEAE-sepharose | 756 | 17.19 | 43.98 | 164 | 52 |
| CM-sepharose | 459 | 0.71 | 646 | 2,421 | 32 |
| Mono SHR 5/5 | 413 | 0.12 | 3,457 | 12,950 | 28 |

Example 4

Characteristics of Phytase

Figure 3:
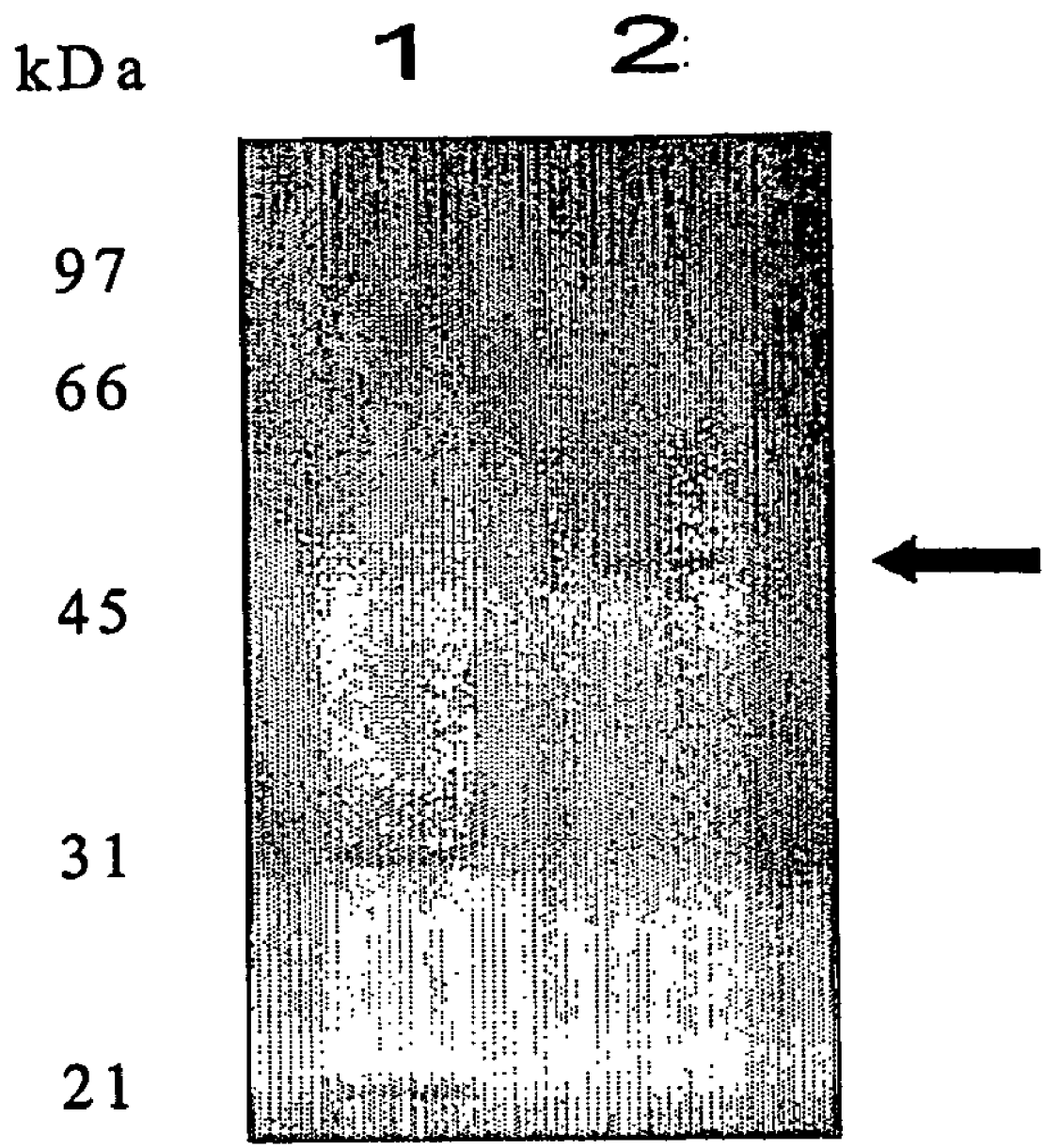
FIG. 3 is an electrophoresis photograph showing the result of SDS-PAGE with phytase produced from *Citrobacter braakii* YH-15, Lane 1: Marker, Lane 2: Purified phytase

<4-1> Determination of Molecular Weight and N-terminal Amino Acid Sequence of Phytase The present inventors measured molecular weight of the purified phytase by SDS-PAGE electrophoresis. In FIG. 3, lane 1 was marker protein whose size was known, lane 2 was the final phytase protein purified through chromatography using Mono S column. From the measurement, phytase of the present invention was confirmed to have molecular weight of about 47,000 Da.

N-terminal amino acid sequence of the phytase protein of the present invention was examined by using protein/peptide sequencer (Applied Biosystem, USA), resulting in the confirmation that N-terminal had an amino acid sequence represented by SEQ. ID. No 2. N-terminal sequence represented by SEQ. ID. No 2 was compared with N-terminal sequences of Eschelichia coli originated phytase enzyme (R. Greiner, et al., Arch. Biochem. Biophys. 1993, 303, 107-113), Aspergillus ficuum (A. H. Ullah, et al., Prep. Biochem. 1988, 18, 443-458) originated phytase enzyme and Bacillus sp. originated phytase enzyme (Y. O. Kim, et al., FEMS Microbiol Lett, 1998, 162, 185-191), resulting in no similarity among them (Table 4). Therefore, phytase produced by Citrobacter braakii YH-15 of the present invention was confirmed to be a novel enzyme.

TABLE 4

Comparison of N-terminal amino acid sequences of the novel enzyme and conventional enzymes

| Enzyme | N-terminal amino acid sequence |
|---|---|
| Citrobacter braakii YH-15 originated phytase | SEQ. ID. No 2 (E-E-Q-N-G-M-K-L-E-R) |
| Eschelichia coli originated phytase | SEQ. ID. No 3 (S-E-P-E-L-K-L-E-N-A-V-V) |
| Aspergillus ficuum originated phytase | SEQ. ID. No 4 (F-S-Y-G-A-A-I-P-Q-S-T-Q-E-K-Q) |
| Bacillus sp. originated phytase | SEQ. ID. No 5 (S-D-P-Y-H-F-T-V-N-A-A-X-E-T-E) |

<4-2> Enzyme Activity of Phytase According to Temperature and pH

The present invention investigated an enzyme activity of phytase, according to temperature and pH, purified through chromatography using Mono S column.

Figure 4:
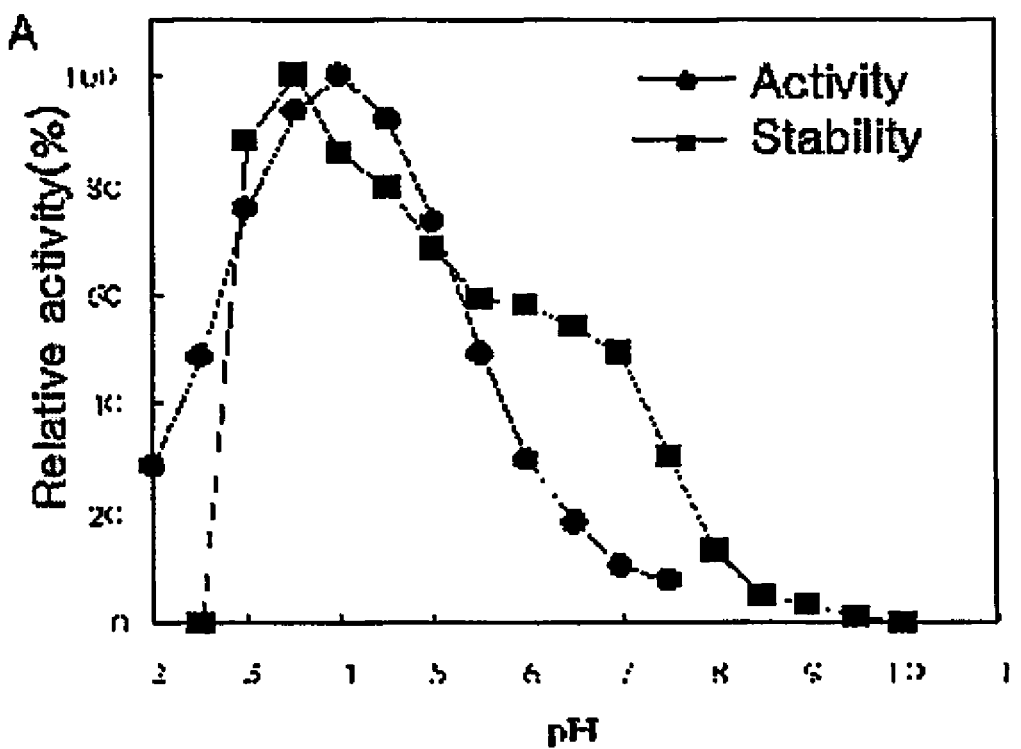
FIG. 4 is a set of graphs showing the biochemical characteristics of phytase produced from *Citrobacter braakii* YH-15, A: Relative activity according to pH,
B: Relative activity according to temperature
Figure 4:
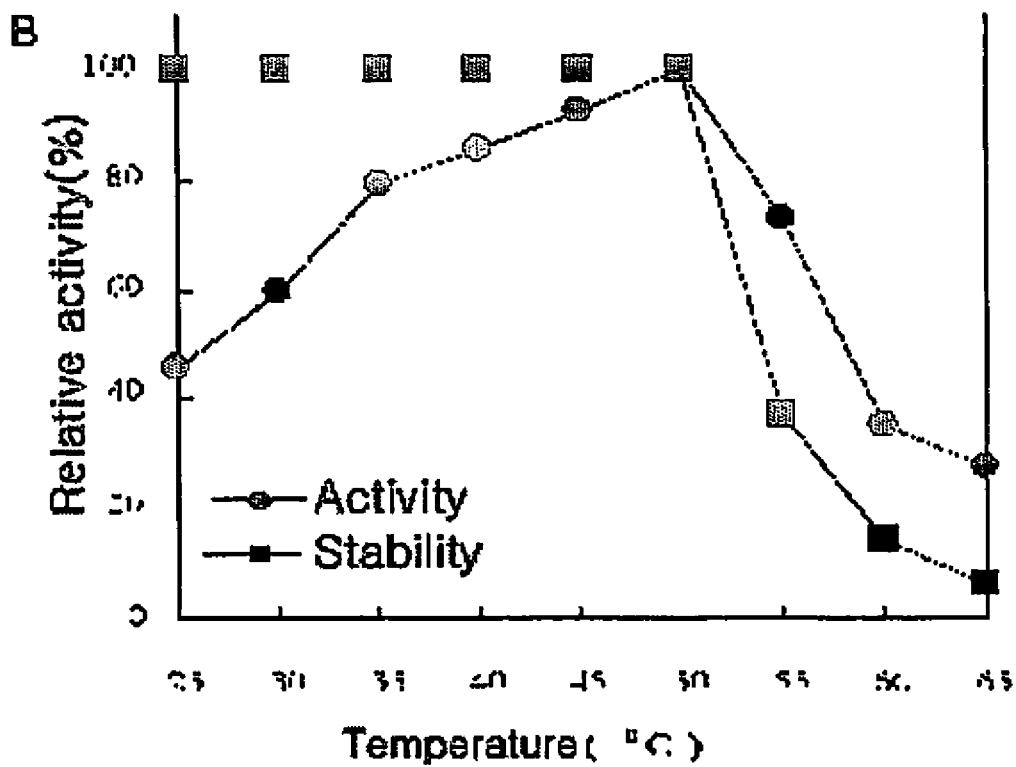

FIG. 4A shows the enzyme activity varied with temperature. The highest activity was observed at 50° C. The activity was stably maintained at 50° C. for 1 hour. When the enzyme was left at 55° C. for 10 minutes, 75% of the activity was still remained.

FIG. 4B shows the enzyme activity varied with pH. The highest activity was observed at pH 4.0. 50% of the enzyme activity was still maintained at pH 2.5. The activity was very stably maintained at 37° C., at pH 3.0-4.5 for 7 days, and 50% activity still remained at pH 7.0. But, as the protein was left under pH 3.0 for 4 hours, the enzyme activity was almost lost. From temperature and pH test with the protein, phytase of the present invention was believed to be very suitable for being used as a feed additive for monogastric animals.

<4-3> Enzyme Activity of Phytase According to Metal Ions and Inhibitors

The present inventors investigated the effect of metal ions and inhibitors on the enzyme activity of phytase of the present invention. Among various metal ions, the enzyme activity of the protein was strongly inhibited by $Fe^{3+}$, $Zn^{2+}$ and $Cu^{2+}$ under the concentration of 10 mM and was inhibited 50% by NaCl at the concentration of 1 M (Table 5).

As for inhibitors, the enzyme activity was hardly affected by dithothreitol and 2-mercaptoethanol involved in disulfate bond. But, as the protein was left at 37° C. for 2 hours with 8 M urea or 0.0024% SDS, the enzyme activity was almost lost.

TABLE 5

Enzyme activity of YH-15 phytase according to metal ions and inhibitors

| Metal ion or inhibitor | Concentration (mM) | Relative activity (%) |
|---|---|---|
| — | | 100 |
| EDTA | 6 | 98 |
| KCl | 6 | 95 |
| $MgCl_2$ | 6 | 71 |
| $ZnSO_4$ | 8 | 33 |
| $FeCl_3$ | 6 | 19 |
| $MnCl_2$ | 6 | 92 |
| $CuSO_4$ | 6 | 38 |
| $NiSO_4$ | 6 | 88 |
| $CaCl_2$ | 6 | 87 |
| $CdCl_2$ | 6 | 101 |
| NaCl | 6 | 102 |
| | 1000 | 54 |

<4-4> Substrate Specificity of Phytase

Substrate specificity of phytase to various phosphate ester compounds was investigated. As shown in Table 6, phytase had a strong ability to decompose phytate specifically, but could hardly decompose other phosphate ester compounds. Km value to sodium phytate was 0.46 mM and Vmax value was 6,027 U/mg.

TABLE 6

Substrate specificity of YH-15 phytase

| Substrate | Relative activity (%) |
|---|---|
| Phytate | 100 |
| p-nitrophenyl phosphate | 11.27 |
| Tetrasodium pyrophosphate | 5.95 |
| ATP | 1.86 |
| ADP | 1.04 |
| Glycerophosphate | 0.57 |
| Glucose-1-phosphate | 0.42 |
| Glucose-6-phosphate | 0.33 |
| Fructose-6-phosphate | 0.75 |
| Mannose-6-phosphate | 0.01 |

<4-5> Effect of Proteases on the Enzyme Activity of Phytase

The present inventors investigated the effect of proteases on the enzyme activity of phytase. Particularly, phytase was left at 37° C. for 2 hours with pepsin and trypsin, resulting in no changes in the enzyme activity. But, as papain, elastase and pancreatin were added, 70~85% of the enzyme activity remained.

The result suggested that phytase could promote coefficient of the enzyme inside monogastric animals owing to its resistance against proteases existed in intestines or stomach.

Example 5

Cloning of Phytase Gene and Base Sequencing of the Same

Oligonucleotide probe was designed on the basis of an amino acid sequence represented by SEQ. ID. No 2 and was synthesized by using a DNA synthesizer (Applied Biosystems ABI 380B DNA synthesizer).

Citrobacter braakii originated chromosomal DNA was separated, which was then digested with restriction enzymes EcoRI and XhoI, EcoRI, SphI, BamHI and HindIII, EcoRI and HindIII, EcoR I and BamH I, and PstI. After electrophoresis, the digested DNA fragments were transferred on nylon membrane.

Figure 5:
FIG. 5 is a photograph showing the result of Southern hybridization with a probe using base sequence of phytase, performed after DNA of *Citrobacter braakii* YH-15 was purified.

Oligonucleotide represented by SEQ. ID. No 8, synthesized above, was labeled with DIG, followed by Southern hybridization. As a result, signals were observed at 7.5 kb as Pst I was used and at 4.5 kb as EcoRI and BamHI were used (FIG. 5).

<5-1> Cloning of Phytase Gene

Citrobacter braakii originated chromosomal DNA was digested with Pst I and only 7.5 kb fragments were separated. After being digested with Pst I again, the above DNA was inserted in pBluscript SK vector (STRATAGENE, USA) pretreated with phosphatase (calf intestinal phosphatase) to transfect E. coli XL1-Blue (STRATAGENE, USA). The transfected strains were smeared on 1.5% agar LB plate supplemented with ampicillin, 1% trypton, 0.5% yeast extract and 0.5% NaCl, after which colonies were transferred onto nylon membrane. Colony hybridization was performed by using the oligonucleotide probe to select colonies showing positive reaction, and plasmids were isolated.

As a result, a 10.5 kb size plasmid containing 7.5 kb DNA insert was confirmed and named pB-phyF.

E. coli XL1-Blue was transfected again with the pB-phyF. Then, phytase activity was measured by the same method as used in the above Example <3-3>. As a result, all of the generated colonies showed phytase activities.

<5-2> Sequence Analysis of a Novel Phytase Gene

Base sequence of pB-phyF separated in the above Example <5-1> was analyzed. At that time, DNA sequencing kit (Big Dye DNA Sequencing kit, Perkin-Elmer, Applied Biosystem) and ABI PRISM DNA sequencer (Perkin-Elmer) were used. The base sequence analyzed by the above automatic sequencer was inputted in DNASTAR amino acid sequence analysis program (DNASTAR, Inc.), by which an open reading frame of phytase represented by SEQ. ID. No 6 composing 1302 bases was determined. The open reading frame was composed of a signal sequence consisting of 22 amino acids and an active phytase consisting of 411 amino acids. The molecular weight of the active phytase without a signal sequence was about 47,000 Da.

The amino acid sequence of a novel phytase obtained above was compared with amino acid sequences recorded in GenBank and SWISSPROT using BLAST program. As a result, it was confirmed that the novel phytase sequence had a very low homology (just 60%) with the sequence originated from Escherichia coli. Therefore, the phytase of the present invention produced by Citrobacter braakii was confirmed to be a novel enzyme.

INDUSTRIAL APPLICABILITY

As explained hereinbefore, Citrobacter braakii of the present invention produces a novel phytase having a strong enzyme activity, comparing to other conventional phytases. Thus, the phytase of the present invention or Citrobacter braakii producing the same can be effectively used as a feed additive for monogastric animals and for the recovery of specific degradation product of phytic acid at low price. In addition, the phytase of the present invention has strong resistance against proteases, so that it maintains high enzyme activity without being decomposed in intestines or stomach after being administered in monogastric animals.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. An isolated or recombinant protein having phytase activity, said protein consisting of the amino acid sequence of SEQ ID NO: 7.

2. The isolated or recombinant protein as set forth in claim 1, wherein the protein is expressed by a polynucleotide comprising the nucleotide sequence of SEQ ID NO: 6.

3. An isolated gene encoding the protein of claim 1.

4. The gene as set forth in claim 3, wherein the gene consists of the polynucleotide sequence of SEQ ID NO: 6.

5. A feed additive containing the protein of claim 1.

6. An isolated gene encoding the protein of claim 2.

7. A feed additive containing the protein of claim 2.

8. An isolated gene encoding a protein having phytase activity, said protein comprising the amino acid residues 23-433 of SEQ ID NO: 7.

9. The isolated gene of claim 8, wherein the protein has the amino acid sequence of SEQ ID NO: 7.

10. The isolated gene of claim 8, wherein the gene comprises the nucleotide sequence of SEQ ID NO: 6.

* * * * *

SEQUENCE LISTING

```
<160> NUMBER OF SEQ ID NOS: 8

<210> SEQ ID NO 1
<211> LENGTH: 1481
<212> TYPE: DNA
<213> ORGANISM: Citrobacter braakii YH-15
<220> FEATURE:
<221> NAME/KEY: MISC_FEATURE
<222> LOCATION: (1134)..(1134)
<223> OTHER INFORMATION: n can be a, c, g or t

<400> SEQUENCE: 1
tagagtttga  tcctggctca  gattgaacgc  tggcggcagg  cctaacacat  gcaagtcgaa     60
cggtagcaca  gaggagcttg  ctccttgggt  gacgagtggc  ggacgggtga  gtaatgtctg    120
ggaaactgcc  cgatggaggg  ggataactac  tggaaacggt  agctaatacc  gcataacgtc    180
gcaagaccaa  agaggggggac  cttcgggcct  cttgccatcg  gatgtgccca  gatgggatta    240
gctagtaggt  ggggtaacgg  ctcacctagg  cgacgatccc  tagctggtct  gagaggatga    300
ccagccacac  tggaactgag  acacggtcca  gactcctacg  ggaggcagca  gtggggaata    360
ttgcacaatg  ggcgcaagcc  tgatgcagcc  atgccgcgtg  tatgaagaag  gccttcgggt    420
tgtaaagtac  tttcagcgag  gaggaaggtg  ttgtggttaa  taccgcagc   aattgacgtt    480 actcgcagaa  gaagcaccgg  ctaactccgt  gccagcagcc  gcggtaatac  ggagggtgca    540
```

```
agcgttaatc ggaattactg ggcgtaaagc gcacgcaggc ggtctgtcaa gtcggatgtg      600
aaatccccgg gctcaacctg gaactgcatc cgaaactggc aggctagagt cttgtagag       660 gggggtagaa ttccaggtgt agcggtgaaa tgcgtagaga tctggaggaa taccggtggc      720
gaaggcggcc ccctggacaa agactgacgc tcaggtgcga aagcgtgggg agcaaacagg      780
attagatacc ctggtagtcc acgccgtaaa cgatgtcgac ttggaggttg tgcccttgag      840
gcgtggcttc cggagctaac gcgttaagtc gaccgcctgg ggagtacggc cgcaaggtta      900
aaactcaaat gaattgacgg gggcccgcac aagcggtgga gcatgtggtt taattcgatg      960
caacgcgaag aaccttacct actcttgaca tccagagaac ttagcagaga tgctttggtg     1020
ccttcgggaa ctctgagaca ggtgctgcat ggctgtcgtc agctcgtgtt gtgaaatgtt     1080
gggttaagtc ccgcaacgag cgcaaccctt atcctttgtt gccagcggtt cggncgggaa     1140
ctcaaaggag actgccagtg ataaactgga ggaaggtggg gatgacgtca agtcatcatg     1200
gcccttacga gtagggctac acacgtgcta caatggcata tacaaagaga agcgacctcg     1260
cgagagcaag cggacctcat aaagtatgtc gtagtccgga ttggagtctg caactcgact     1320
ccatgaagtc ggaatcgcta gtaatcgtgg atcagaatgc cacggtgaat acgttcccgg     1380
gccttgtaca caccgcccgt cacaccatgg gagtgggttg caaaagaagt aggtagctta     1440
accttcggga gggcgcttac ctctttggat tcagatgggg a                         1481
```

<210> SEQ ID NO 2
<211> LENGTH: 10
<212> TYPE: PRT
<213> ORGANISM: Citrobacter braakii YH-15

<400> SEQUENCE: 2

Glu Glu Gln Asn Gly Met Lys Leu Glu Arg
1               5                   10

<210> SEQ ID NO 3
<211> LENGTH: 12
<212> TYPE: PRT
<213> ORGANISM: Escherichia coli

<400> SEQUENCE: 3

Ser Glu Pro Glu Leu Lys Leu Glu Asn Ala Val Val
1               5                   10

<210> SEQ ID NO 4
<211> LENGTH: 15
<212> TYPE: PRT
<213> ORGANISM: Aspergillus ficuum

<400> SEQUENCE: 4

Phe Ser Tyr Gly Ala Ala Ile Pro Gln Ser Thr Gln Glu Lys Gln
1               5                   10                  15

<210> SEQ ID NO 5
<211> LENGTH: 15
<212> TYPE: PRT
<213> ORGANISM: Bacillus sp.
<220> FEATURE:
<221> NAME/KEY: MISC_FEATURE
<222> LOCATION: (12)..(12)
<223> OTHER INFORMATION: Xaa can be any natural amino acid

<400> SEQUENCE: 5

Ser Asp Pro Tyr His Phe Thr Val Asn Ala Ala Xaa Glu Thr Glu

<210> SEQ ID NO 6
<211> LENGTH: 1302
<212> TYPE: DNA
<213> ORGANISM: Citrobacter braakii YH-15
<220> FEATURE:
<221> NAME/KEY: gene
<222> LOCATION: (1)..(1302)
<223> OTHER INFORMATION: phytase gene

<400> SEQUENCE: 6

```
atgagtacat tcatcattcg tttattaatt ttttctctct tatgcggttc tttctcaata    60
catgctgaag agcagaacgg catgaaactg agcgggttg tgatagtgag ccgtcatgga   120
gtaagagcac ctacgaagtt cactccaata atgaaagatg tcacacccga ccaatgccca   180
caatgggatg tgccgttagg atggctaacg cctcgtgggg agaacttgt ttctgaatta   240
ggtcagtatc aacgtttatg gttcacaagc aaaggtctgt tgaataatca aacgtgccca   300
tctccagggc aggttgctgt tattgcagac acggatcaac gcacccgtaa acgggtgag   360
gcgtttctgg ctgggttagc accaaaatgt caaattcaag tgcattatca aaggatgaa   420
gaaaaaaatg atcctctttt taatccggta aaaatgggga atgttcgtt aacacattg    480
aaggttaaaa acgctattct ggaacgggcc ggaggaaata ttgaactgta cccaacgc    540
tatcaatctt catttcggac cctggaaaat gtttaaatt tctcacaatc ggagacatgt   600
aagactacag agaagtctac gaaatgcaca ttaccagagg cttaccgtc tgaatttaag   660
gtaactcctg acaacgtatc attacctggt gcctggagtc tttcttccac gctgactgag   720
atatttctgt tgcaagaggc ccagggaatg ccacaggtag cctgggggcg tattacggga   780
gaaaagaat ggagagattt gttaagtctg cataacgctc agtttgatct tttgcaaaga   840
actccagaag ttgcccgtag tagggccaca ccattactcg atatgataga cactgcatta   900
ttgacaaatg gtacaacaga aaacaggtat ggcataaaat acccgtatc tctgttgttt   960
attgctggtc atgataccaa tcttgcaaat ttaagcgggg ctttagatct taagtggtcg  1020
ctgcccggtc aacccgataa taccctcct ggtggggagc ttgtattcga aaagtggaaa  1080
agaaccagtg ataatacgga ttgggttcag gtttcatttg tttatcagac gctgagagat  1140
atgagggata ttcaaccgtt gtcgttagaa aaacctgctg aaaagttga tttaaaatta  1200
attgcatgtg aagagaaaaa tagtcaggga atgtgttcgt taaaaagttt ttccaggctc  1260
attaaggaaa ttcgcgtgcc agagtgtgca gttacggaat aa                    1302
```

<210> SEQ ID NO 7
<211> LENGTH: 433
<212> TYPE: PRT
<213> ORGANISM: Citrobacter braakii YH-15
<220> FEATURE:
<221> NAME/KEY: PEPTIDE
<222> LOCATION: (1)..(433)
<223> OTHER INFORMATION: phytase

<400> SEQUENCE: 7

```
Met Ser Thr Phe Ile Ile Arg Leu Leu Ile Phe Ser Leu Leu Cys Gly
  1               5                  10                  15

Ser Phe Ser Ile His Ala Glu Glu Gln Asn Gly Met Lys Leu Glu Arg
             20                  25                  30

Val Val Ile Val Ser Arg His Gly Val Arg Ala Pro Thr Lys Phe Thr
         35                  40                  45
```

```
Pro Ile Met Lys Asp Val Thr Pro Asp Gln Trp Pro Gln Trp Asp Val
 50                  55                  60
Pro Leu Gly Trp Leu Thr Pro Arg Gly Gly Glu Leu Val Ser Glu Leu
 65                  70                  75                  80
Gly Gln Tyr Gln Arg Leu Trp Phe Thr Ser Lys Gly Leu Leu Asn Asn
                 85                  90                  95
Gln Thr Cys Pro Ser Pro Gly Gln Val Ala Val Ile Ala Asp Thr Asp
            100                 105                 110
Gln Arg Thr Arg Lys Thr Gly Glu Ala Phe Leu Ala Gly Leu Ala Pro
        115                 120                 125
Lys Cys Gln Ile Gln Val His Tyr Gln Lys Asp Glu Lys Asn Asp
    130                 135                 140
Pro Leu Phe Asn Pro Val Lys Met Gly Lys Cys Ser Phe Asn Thr Leu
145                 150                 155                 160
Lys Val Lys Asn Ala Ile Leu Glu Arg Ala Gly Asn Ile Glu Leu
                165                 170                 175
Tyr Thr Gln Arg Tyr Gln Ser Ser Phe Arg Thr Leu Glu Asn Val Leu
            180                 185                 190
Asn Phe Ser Gln Ser Glu Thr Cys Lys Thr Thr Glu Lys Ser Thr Lys
        195                 200                 205
Cys Thr Leu Pro Glu Ala Leu Pro Ser Glu Phe Lys Val Thr Pro Asp
    210                 215                 220
Asn Val Ser Leu Pro Gly Ala Trp Ser Leu Ser Ser Thr Leu Thr Glu
225                 230                 235                 240
Ile Phe Leu Leu Gln Glu Ala Gln Gly Met Pro Gln Val Ala Trp Gly
                245                 250                 255
Arg Ile Thr Gly Glu Lys Glu Trp Arg Asp Leu Leu Ser Leu His Asn
            260                 265                 270
Ala Gln Phe Asp Leu Leu Gln Arg Thr Pro Glu Val Ala Arg Ser Arg
        275                 280                 285
Ala Thr Pro Leu Leu Asp Met Ile Asp Thr Ala Leu Leu Thr Asn Gly
    290                 295                 300
Thr Thr Glu Asn Arg Tyr Gly Ile Lys Leu Pro Val Ser Leu Leu Phe
305                 310                 315                 320
Ile Ala Gly His Asp Thr Asn Leu Ala Asn Leu Ser Gly Ala Leu Asp
                325                 330                 335
Leu Lys Trp Ser Leu Pro Gly Gln Pro Asp Asn Thr Pro Pro Gly Gly
            340                 345                 350
Glu Leu Val Phe Glu Lys Trp Lys Arg Thr Ser Asp Asn Thr Asp Trp
        355                 360                 365
Val Gln Val Ser Phe Val Tyr Gln Thr Leu Arg Asp Met Arg Asp Ile
    370                 375                 380
Gln Pro Leu Ser Leu Glu Lys Pro Ala Gly Lys Val Asp Leu Lys Leu
385                 390                 395                 400
Ile Ala Cys Glu Glu Lys Asn Ser Gln Gly Met Cys Ser Leu Lys Ser
                405                 410                 415
Phe Ser Arg Leu Ile Lys Glu Ile Arg Val Pro Glu Cys Ala Val Thr
            420                 425                 430
Glu

<210> SEQ ID NO 8
<211> LENGTH: 30
<212> TYPE: DNA
<213> ORGANISM: Artificial Sequence
```

-continued

```
<220> FEATURE:
<223> OTHER INFORMATION: primer for the detection of phytase gene

<400> SEQUENCE: 8
gargarcaga ayggyatgaa actggarcgy                                     30
```